United States Patent
Wang et al.

(10) Patent No.: US 8,372,332 B2
(45) Date of Patent: *Feb. 12, 2013

(54) FABRICATING AN IMPLANTABLE MEDICAL DEVICE FROM AN AMORPHOUS OR VERY LOW CRYSTALLINITY POLYMER CONSTRUCT

(75) Inventors: Yunbing Wang, Sunnyvale, CA (US); Lothar Kleiner, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 12/465,570

(22) Filed: May 13, 2009

(65) Prior Publication Data
US 2010/0252965 A1 Oct. 7, 2010

Related U.S. Application Data

(63) Continuation-in-part of application No. 12/189,620, filed on Aug. 11, 2008.

(51) Int. Cl.
*B29C 49/04* (2006.01)
*B29C 49/64* (2006.01)
*B29C 49/08* (2006.01)

(52) U.S. Cl. ........ 264/564; 264/534; 264/535; 264/540; 264/567; 264/573; 264/346

(58) Field of Classification Search .......... 264/514, 264/515, 523, 534, 540, 563, 564, 567, 171.26, 264/178 R, 209.1, 209.3, 209.4, 209.5, 211, 264/211.13, 235, 346, 519–521, 532, 535, 264/573

See application file for complete search history.

(56) References Cited

U.S. PATENT DOCUMENTS

| | | | |
|---|---|---|---|
| 5,211,902 A * | 5/1993 | Unger et al. | 264/296 |
| 6,319,576 B1 | 11/2001 | Rule et al. | |
| 6,932,930 B2 * | 8/2005 | DeSimone et al. | 264/235 |
| 2003/0083732 A1 | 5/2003 | Stinson | |
| 2004/0181271 A1 | 9/2004 | Desimone et al. | |
| 2006/0246108 A1 | 11/2006 | Pacetti et al. | |
| 2007/0038290 A1 * | 2/2007 | Huang et al. | 623/1.16 |
| 2007/0132156 A1 * | 6/2007 | Burgermeister et al. | 264/479 |
| 2007/0200271 A1 * | 8/2007 | Dave | 264/211 |
| 2007/0253996 A1 | 11/2007 | Bin et al. | |

(Continued)

FOREIGN PATENT DOCUMENTS
EP 1 872 808 1/2008
WO WO 2007/142736 12/2007

(Continued)

OTHER PUBLICATIONS

Brostow, Witold; Performance of Plastics; Dec. 2000; Hanser Gardner Publications; 1st edition, pp. 254-255.*

(Continued)

*Primary Examiner* — Joseph Del Sole
*Assistant Examiner* — Ryan Ochylski
(74) *Attorney, Agent, or Firm* — Squire Sanders (US) LLP

(57) ABSTRACT

Methods of fabricating a polymeric implantable device with improved fracture toughness through annealing, nucleating agents, or both are disclosed herein. A polymeric construct that is completely amorphous or that has a very low crystallinity is annealed with no or substantially no crystal growth to increase nucleation density. Alternatively, the polymer construct includes nucleating agent. The crystallinity of the polymer construct is increased with a high nucleation density through an increase in temperature, deformation, or both. An implantable medical device, such as a stent, can be fabricated from the polymer construct after the increase in crystallinity.

9 Claims, 4 Drawing Sheets

U.S. PATENT DOCUMENTS

| | | | |
|---|---|---|---|
| 2007/0253999 | A1 | 11/2007 | Huang et al. |
| 2007/0283552 | A1* | 12/2007 | Gale et al. ................ 29/515 |
| 2008/0014240 | A1 | 1/2008 | Gale et al. |
| 2008/0051873 | A1 | 2/2008 | Cottone et al. |
| 2008/0177374 | A1* | 7/2008 | Zheng et al. ............ 623/1.15 |
| 2009/0248147 | A1 | 10/2009 | Wang |
| 2010/0025894 | A1* | 2/2010 | Kleiner et al. ............ 264/528 |
| 2010/0036478 | A1 | 2/2010 | Wang et al. |
| 2010/0038822 | A1* | 2/2010 | Wang et al. ............... 264/294 |

FOREIGN PATENT DOCUMENTS

| | | |
|---|---|---|
| WO | WO 2008/008495 | 1/2008 |
| WO | WO 2010/017090 | 2/2010 |
| WO | WO 2010/019478 | 2/2010 |

OTHER PUBLICATIONS

International Search Report for PCT/US2009/053029, mailed Aug. 12, 2010, 8 pgs.

Anderson et al., "Melt preparation and nucleation efficiency of polylactide stereocomplex crystallites", Polymer 47, pp. 2030-2035 (2006).

Borokhovskii et al., "Thermodynamic analysis of nucleus formation in crystallization of polymers", Vysokomol. Soyed. A18, No. 11, pp. 2406-2411 (1976).

Schmidt et al., "Polylactide stereocomplex crystallites as nucleating agents for isotactic polylactide", J. of Pol. Science vol. 39, pp. 300-313 (2001).

International Search Report for PCT/US2010/034077, mailed Jan. 20, 2011, 6 pgs.

Van Vlack, "Elements of Materials Science and Engineering", Addison-Wesley Pub. Co., pp. 270-271 (1989).

International Search Report for PCT/US2009/053182, mailed Nov. 9, 2009, 7 pgs.

Brizzolara et al., "Mechanism of the Stereocomplex Formation between Enantiomeric Poly(lactide)s", Macromolecules, vol. 29, pp. 191-197 (1996).

Kawamoto et al., "Nucleating-Agent for Poly(L-lactic acid)-An Optimization of Chemical Structure of Hydrazide Compound for Advanced Nucleation Ability", J. of Applied Polymer Science, vol. 103, pp. 198-203 (2007).

Krouse et al., "Stereocomplex Formation between Enantiomeric Poly(lactides)", Macromolecules, vol. 20, pp. 904-906 (1987).

Takasaki et al., "Development of Stereocomplex Crystal of Polylactide in High-Speed Melt Spinning and Subsequent Drawing and Annealing Processes", Journal of Macromolecular Science: Part B—Physics, vol. B42, Nos. 3 & 4, pp. 403-420 (2003).

Tsuji et al., "Stereocomplex Formation between Enantiomeric Poly(lactic acid)s. 2. Stereocomplex Formation in Concentrated Solutions", Macromolecules, vol. 24, pp. 2719-2724 (1991).

Tsuji et al., "In vitro hydrolysis of blends from enantiomeric poly(lactide)s. Part 4: well-homo-crystallized blend and nonblended films", Biomaterials, vol. 24, pp. 537-547 (2003).

Urayama et al., "Controlled crystal nucleation in the melt-crystallization of poly(L-lactide) and poly(L-lactide)/poly(D-lactide) stereocomplex", Polymer, vol. 44, pp. 5635-5641 (2003).

Yash Khanna, "Rheological Mechanism and Overview of Nucleated Crystallization Kinetics", macromolecules, vol. 26, pp. 3639-3643 (1993).

\* cited by examiner

FABRICATING AN IMPLANTABLE MEDICAL DEVICE FROM AN AMORPHOUS OR VERY LOW CRYSTALLINITY POLYMER CONSTRUCT

This is a continuation-in-part of application Ser. No. 12/189,620 filed on Aug. 11, 2008.

BACKGROUND OF THE INVENTION

1. Field of the Invention

This invention relates to methods of manufacturing polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating the device in whole or in part from materials that erode or disintegrate through exposure to conditions within the body. Thus, erodible portions of the device can disappear or substantially disappear from the implant region after the treatment regimen is completed. After the process of disintegration has been completed, no portion of the device, or an erodible portion of the device will remain. In some embodiments, very negligible traces or residue may be left behind. Stents fabricated from biodegradable, bioabsorbable, and/or bioerodable materials such as bioabsorbable polymers can be designed to completely erode only after the clinical need for them has ended.

SUMMARY OF THE INVENTION

Various embodiments of the present invention include a method of making a stent comprising: annealing a polymeric tube in a temperature range that allows nuclei formation within the polymer with no or substantially no growth of crystallite around the nuclei, wherein the polymer construct has a crystallinity of less than 5% prior to the annealing; growing crystallites around the nuclei after the annealing to obtain a desired crystallinity; and fabricating a stent from the tube after obtaining the desired crystallinity.

Further embodiments of the present invention include A method of making a stent comprising: forming a polymeric tube comprising nucleating agent particles dispersed within the polymer, wherein crystal growth is minimized or prevented during formation of the tube so that the polymer of the formed tube has a crystallinity of less than 5%; after forming the polymeric tube, inducing and allowing crystal growth around the nucleating agent particles dispersed within the polymeric tube to obtain a desired crystallinity; and fabricating a stent from the tube after the crystal growth.

Additional embodiments of the present invention include a method of making a stent comprising: fabricating a polymeric tube with an extrusion process having a crystallinity less than 5% at a temperature below the Tg of the polymer; radially deforming the fabricated polymer tube, wherein the radial deformation increases the degree of crystallinity of the polymer tube to between 15 to 50%; and fabricating a stent from the deformed tube.

DETAILED DESCRIPTION OF THE INVENTION

Various embodiments of the present invention relate to manufacture of polymeric implantable medical devices. In particular, the embodiments include making an implantable medical device from a polymer construct that is amorphous or that has a very low crystallinity. The methods described herein are generally applicable to any polymeric implantable medical device. In particular, the methods can be applied to tubular implantable medical devices such as self-expandable stents, balloon-expandable stents, and stent-grafts.

Figure 1:
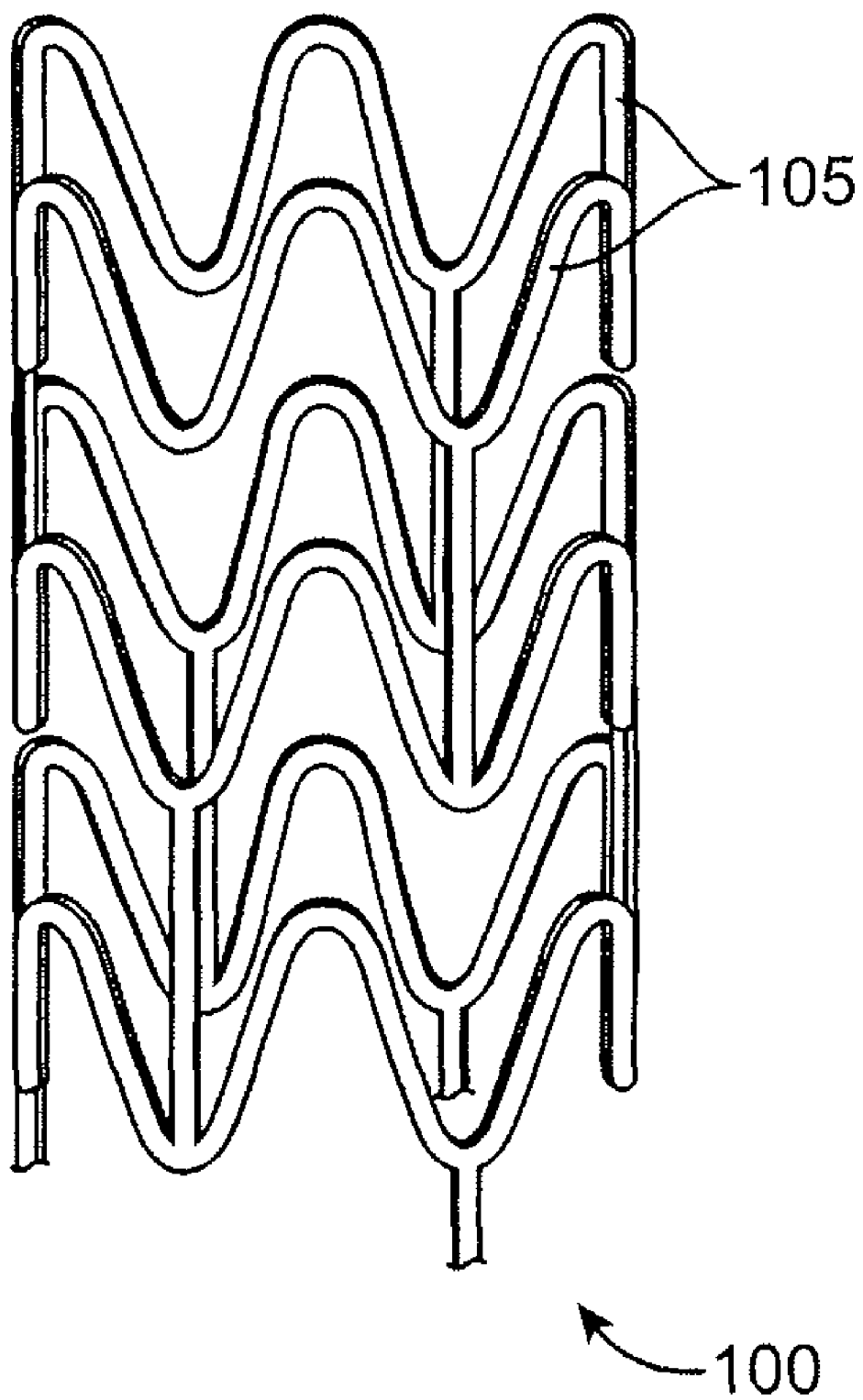
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from several months to a few years. The duration is typically up to about six months, twelve months, eighteen months, or two years. In some situations, the treatment period can extend beyond two years.

As indicated above, a stent has certain mechanical requirements such as high radial strength, high modulus, and high fracture toughness. A stent that meets such requirements greatly facilitates the delivery, deployment, and treatment of a diseased vessel. With respect to radial strength, a stent must have sufficient radial strength to withstand structural loads, namely radial compressive forces, imposed on the stent as it supports the walls of a vessel. In addition, the stent must possess sufficient flexibility to allow for crimping, expansion, and cyclic loading. A polymeric stent with inadequate radial strength can result in mechanical failure or recoil inward after implantation into a vessel.

The strength to weight ratio of polymers is usually smaller than that of metals. To compensate for this, a polymeric stent can require significantly thicker struts than a metallic stent, which results in an undesirably large profile. One way of addressing the strength deficiency of polymers is to fabricate a stent from a deformed polymer construct. Deforming polymers tends to increase the strength along the direction of deformation, which is believed to be due to the induced polymer chain orientation along the direction of deformation. For example, radial expansion of a tube provides preferred circumferential polymer chain orientation in the tube. Additionally, stretching a tube provides preferred axial orientation of polymer chains in the tube. Thus, a stent fabrication process can include radially deforming a polymer tube and cutting a stent from the deformed tube.

With respect to toughness, a polymer stent should also have a high resistance to fracture. Semicrystalline polymers such as poly(L-lactide) (PLLA) that are suitable as stent materials tend to be brittle under biological conditions or conditions within a human body. Specifically, such polymers can have a glass transition temperature (Tg) above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

A number of strategies may be employed to improve the fracture toughness of semicrystalline polymers such as PLLA. For example, a rubbery phase (or toughening agent) may be incorporated in the rigid polymer, such as polycaprolactone or polytrimethylcarbonate through chemical reaction or physical blending. However, this results in decreased strength and modulus. Alternatively, fracture toughness can be improved by reducing the size of the polymer crystals and increasing the density of the nuclei from which the crystals grow.

Generally, in the crystallization of polymers, there are two separate events that occur. The first event is the formation of nuclei in the polymer matrix. The second event is growth of the crystallite around these nuclei. The overall rate of crystallization of the polymer is dependent, therefore, on the equilibrium concentration of nuclei in the polymer matrix, and on the rate of growth of crystallites around these nuclei.

Semicrystalline polymers can contain both amorphous and crystalline domains at temperatures below the melting point. Amorphous regions are those in which polymer chains are in relatively disordered configurations. Crystalline domains or crystallites are those in which polymer chains are in ordered configurations with segments of polymer chains essentially parallel to one another.

The classical view of polymer crystallization is a thermodynamically "frustrated" nucleation and growth process. The transition from the disordered rubber-like state where flexible chains adopt the random coil conformation to a rigid, ordered, three-dimensional state has been formally treated as a classical first-order transition. Crystallites form at the stable nuclei and grow by reorganizing random coil chains into chain-folded crystalline lamellae (ca. 10 nm thick, although the actual thickness depends upon the polymer and crystallization conditions). Chain-folded crystallites form under quiescent conditions. Strain-induced crystallization is more complex and there may be a mixture of extended chain crystals mixed with chain-folded ones. However, individual segments of polymer molecules are often unable to adopt the thermodynamically desirable conformation state necessary for crystallization before adjacent segments crystallize, locking in non-equilibrium amorphous structure. Thus, semicrystalline polymers form a mixture of ordered crystalline and disordered amorphous regions Even the crystalline region represents a distribution of crystallite sizes, which results in a melting point distribution. The broader the distribution, the broader is the distribution of crystallite sizes in the crystalline region. This is unlike metals which exhibit a sharp melting peak because the crystallite size is more uniform). The crystalline lamellae form sheaf-like stacks a few lamellae thick (~50 to 100 nm) that splay and branch as they grow outward, forming spherulites varying from submicron to millimeters in size. The growth of an individual spherulite ceases when it impinges with neighboring spherulites. Only in the theoretical limit of infinite time at the equilibrium melting temperature could a semicrystalline polymer form the thermodynamic ideal single-crystal structure.

Hence, for all practical situations, semicrystalline polymers assume a kinetically-driven, non-equilibrium morphology in the solid state. The overall crystallization kinetics follows the general mathematical formulation that has been developed for the kinetics of phase changes with only minor modifications. The importance of nucleation processes in polymer crystallization has been amply recognized and is based on very general considerations. This concept has been applied to the analysis of the kinetics of polymer crystallization.

Figure 2:
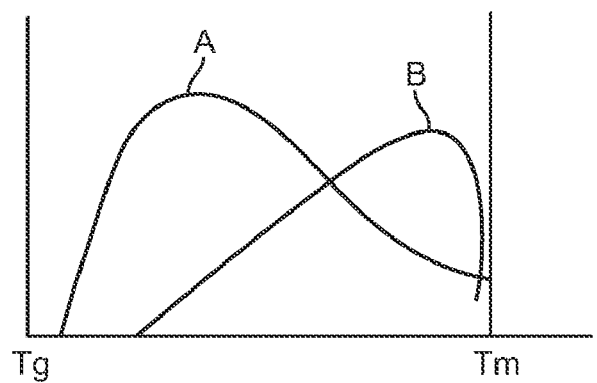
FIG. 2 depicts a schematic plot of the crystal nucleation rate and the crystal growth rate for a polymer.

In general, crystallization tends to occur in a polymer at temperatures between Tg and Tm of the polymer. FIG. 2 shows a schematic of the dependence of nucleation rate (A) and crystal growth rate (B) on temperature between the glass transition temperature (Tg) and the melting temperature (Tm) under quiescent conditions. At temperatures above Tg but far below Tm where polymer chain mobility is limited, nucleation is substantially favored over growth, since the latter process requires much more extensive chain mobility. These nuclei remain present in the polymer until its temperature is elevated above Tm for a period of time. A consequence of the behavior illustrated in FIG. 2 is that at high temperatures there are relatively few, large crystallites formed, while at low temperatures, there are relatively more numerous, smaller crystallites formed.

Various embodiments of the present invention include fabricating a polymeric implantable medical device having a high nucleation density, small crystallite size, and a certain degree of crystallinity to provide a high fracture toughness and strength. The fabrication of the device having high fracture toughness and strength is achieved through a synergistic combination of process steps.

In these embodiments, the process steps include obtaining or fabricating a polymer construct that is completely amorphous (100% amorphous, 0% crystallinity) or with very low crystallinity, such as less than 5% crystallinity. In exemplary embodiments, the crystallinity of the construct can be 1-2%, 3-4%, or 4-5%. In some other embodiments the crystallinity of the construct can greater than 5%, for example between 5-10%, however, a crystallinity of less than 5% is preferred and is expected to result in superior mechanical properties of a device fabricated from the construct.

The fabrication of the device includes processing the polymer construct to increase the crystallinity to a desired level in a controlled manner resulting in a high nucleation density and a small uniform crystallite size distribution. The crystallinity of the amorphous or very low crystallinity construct is increased by increasing the temperature of the construct from below the Tg of the polymer to a crystallization temperature range of the polymer, by deforming the construct, or both.

The increase in temperature and deformation induce crystal growth in the polymer construct. In a deformation process, crystallite growth is likely temperature-induced as well, however the strain or stress induced crystallization is a much faster process than quiescent crystallization.

Deformation, which can be accompanied by an increase in temperature, is the preferred method of crystal growth, particularly in fabricating devices such as stents. The deformation can include radial expansion of a tube (which induces preferred uniaxial circumferential orientation of polymer chains in the tube) or both radial expansion and axial elongation (inducing biaxial orientation of chains). The uniaxial/biaxial orientation provide high strength and fracture toughness to the stent which is essential to the proper functioning of the stent. The uniaxial/biaxial orientation can provide high strength and fracture toughness that may not be provided by crystallinity in the absence of uniaxial/biaxial orientation.

Deformation serves the dual purpose of increasing crystallinity and inducing orientation. The embodiments of the present invention provide a method of imparting the desired or a significant portion of the desired crystallinity and uniaxial/biaxial orientation in a single process step or at the same time, which is a significant advantage. Since inducing orientation increases crystallinity, the two features are much more readily controlled when performed in the same process step.

The processing step to increase the crystallinity is performed after formation of the construct since the processing step can achieve a high nucleation density and a controlled growth of crystallites with a small crystal and relatively uniform size distribution. In addition, the deformation is employed not only to increase crystallinity, but to impart a controllable uniaxial or biaxial orientation to polymer chains in the construct. The orientation improves radial strength and fracture toughness that can be essential for the proper functioning of a device such as a stent. A high nucleation density with a small crystal size and relatively uniform distribution and controllable biaxial chain orientation is difficult to achieve when forming the construct with conventional melt processing techniques such as extrusion or injection molding.

In certain embodiments, the high nucleation density can be achieved through the presence of nucleating agents in the polymer construct when processed to increase crystallinity and polymer chain orientation. In other embodiments, the high nucleation density is achieved through an annealing step, described below, performed prior to the processing to increase the crystallinity and polymer chain orientation. Additionally, in some embodiments, both the nucleating agents and the annealing step can be employed to achieve high nucleation density.

A polymer construct can be a polymer or polymer material formed into a geometrical shape, such as a tube or a sheet. The shape is chosen so that further processing can be applied to form an implantable medical device. For example, the polymer construct can be a tube and a stent pattern can be cut into the tube to form a stent. The polymer construct can be formed using a melt processing technique, such as extrusion or injection molding. Alternatively, a polymer tube may be formed from a sheet that is rolled and bonded into a tube. The deformation in the case of tube can include radial expansion, axial elongation, or both.

As indicated above, in some embodiments, processing of the construct can be achieved by including nucleating agents in the polymer construct. Nucleating agents are insoluble low molecular weight additives which provide nuclei for heterogeneous crystallization and therefore, increase nucleation density in a polymer. Since they raise the nucleation density, smaller and more crystallites or spherulites are produced. Examples of nucleating agents are metal salts, organic acids, and inorganic fillers. Specific examples include ethylenebis (12-hydroxystearylamide), cyclohexanedicarboxylic dianilide, and tetramethylenedicarboxylic disalicyloylhydrazide. For a more comprehensive list, see for example *Performance of Plastics* by Witold Brostow, Hanser Publishers (April 2000).

In these embodiments, nucleating agent particles may be mixed or dispersed within the polymer construct. The nucleating agents may have poor compatibility with the polymer, therefore, at high enough concentrations, poor mechanical properties could result, which would be detrimental to the performance of a device, such as stent. In exemplary embodiments, the concentration of nucleating agents is preferred to be less than about 2 wt %. In more preferred embodiments, the concentration is between 0.01-0.5 wt %. In some embodiments, the nucleating agent can be incorporated into the polymer construct when it is formed by a melt processing technique, such as extrusion or injection molding. For example, the nucleating agent can be fed into an extruder and mixed with the polymer. The process of making an amorphous or very low crystallinity polymer construct includes making the construct with a nucleating agent or making a construct that is free of nucleating agent, as described below.

In other embodiments of the present invention, fabricating a polymeric device can include a step of annealing an amorphous or very low crystallinity polymer construct with no or substantially no crystal growth to increase nucleation density. The method further includes the step of increasing crystallinity by growing crystallites around the formed nuclei after the annealing step. As described in more detail below, the crystallite growth step can be performed by increasing the temperature of the construct, deforming the construct, or both.

Figure 3A:
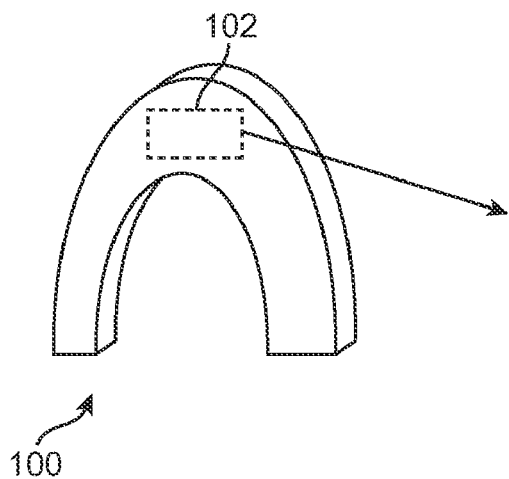
FIG. 3A depicts a strut of a polymeric stent fabricated without annealing.
Figure 3B:
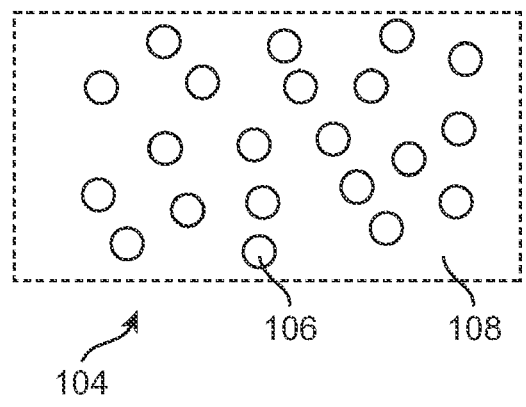
FIG. 3B is a schematic microstructure of a section of the strut of FIG. 3A.
Figure 4A:
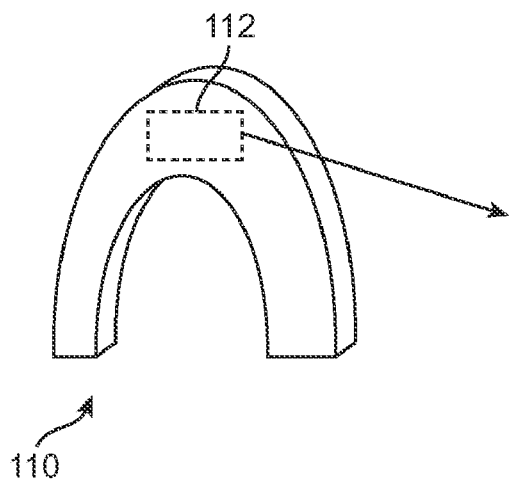
FIG. 4A depicts a strut of a polymeric stent fabricated with annealing.
Figure 4B:
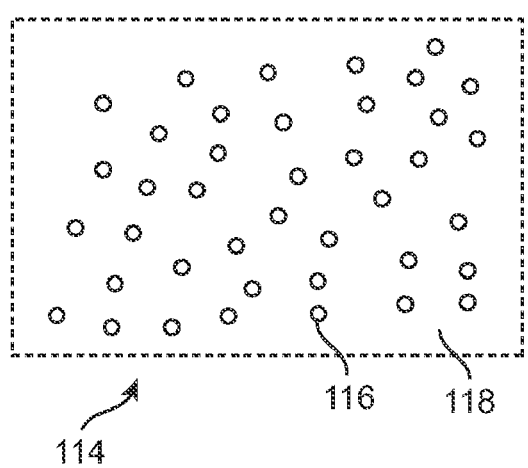
FIG. 4B is a schematic microstructure of a section of the strut of FIG. 4A.

FIG. 3A depicts a strut 100 of a polymeric stent fabricated without annealing or use of nucleating agent and FIG. 3B is a schematic microstructure 104 of a section 102 of strut 100 showing a small amount of large crystals 106 dispersed within an amorphous region 108. FIG. 4A depicts strut 110 of a polymeric stent fabricated with annealing, nucleating agent, or both. FIG. 4B depicts the schematic microstructure 114 of a section 112 of strut 110 showing a large amount of smaller crystals 116 dispersed within an amorphous region 118.

In the annealing embodiments, the annealing step can include annealing a polymer construct at a temperature or temperature range for a selected annealing time that allows nuclei formation within the polymer with no or substantially no growth of crystallites around the nuclei. The annealing seeds nuclei throughout the polymer construct. The temperature range of annealing is preferred to be between Tg and Tg+25° C., or more preferred to be between Tg+5° C. to Tg+15° C. to obtain a certain amount of nuclei while prevent crystal growth. The use of nucleating agents rather than the annealing is analogous in that the nucleating agents are seeded throughout the polymer construct.

Exemplary semicrystalline polymers that may be used in embodiments of the present invention include PLLA, poly(D-lactide) (PDLA), polyglycolide (PGA), (poly(L-lactide-co-glycolide) (PLGA), (poly(L-lactide-co-caprolactone) (PLCL), and PLLA-b-poly(ethylene oxide) (PLLA-b-PEO). Literature values of ranges of Tg and Tm of PLLA and PGA are given in Table 1.

TABLE 1

Tg and Tm for PLLA and PGA.

| Polymer | Melting Point (° C.)[1] | Glass Transition Temp (° C.)[1] |
|---------|-------------------------|-------------------------------|
| PGA     | 225-230                 | 35-40                         |
| PLLA    | 173-178                 | 60-65                         |

[1]Medical Plastics and Biomaterials Magazine, March 1998.

The annealing time can be up to 5 min, 10 min, 30 min, 1 hr, or greater than 1 hr. The annealing time can be selected to obtain a desired nucleation density.

As indicated above, after the annealing time, embodiments of the method further include a crystal growth step, which preferably includes deformation to impart chain orientation, of growing crystallites around the nuclei to obtain a desired crystallinity and polymer chain orientation in the polymer construct that is free of nucleating agent. Alternatively, the method includes a crystal growth step, which also preferably includes deformation to impart polymer chain orientation, for a polymer construct with nucleating agent without the prior annealing step. In another alternative embodiment, a polymer construct with nucleating agent can be subjected to an annealing step prior to the deformation which results in crystal growth and polymer chain orientation. In this last embodiment, the polymer construct will include both nuclei and nucleating agent particles that are seeds for growth of crystallites.

A desired final crystallinity of the construct may be at least 10%, 10-20%, 20-30%, 30-40%, 40-50%, or greater than 50%. However, a crystallinity above 50% may result in fracture toughness that is too low, i.e., brittle behavior that could result in fracture during crimping, deployment, and after deployment of a stent. A crystallinity of 15 to 50% is expected to provides adequate to superior strength and fracture toughness for a PLLA stent scaffolding.

The crystallinity of the construct subjected to the annealing step, but free of nucleating agent, can include a contribution from the crystallites grown around the nuclei formed from the annealing and a contribution from crystallites grown from crystallites and nuclei present in the construct prior to the annealing. The crystallinity of the construct with nucleating agent can include a contribution from the crystallites grown around the nucleating agent and a contribution from crystallites grown from crystallites and nuclei present in the construct after its formation. The crystallinity of the construct subjected to the annealing step and with nucleating agent can include a contribution from crystallites grown around the nuclei, from the crystallites grown around the nucleating agent, and a contribution from crystallites grown from crystallites and nuclei present in the construct prior to the annealing.

After the crystallite growth step that preferably includes the deformation to impart orientation, the construct can then be subjected to further processing steps in the device fabrication process. For example, a stent pattern can be cut into the tube.

In certain embodiments, the temperature of the polymer construct during deformation can be higher than the annealing temperature range, but lower than Tm. In such embodiments, growth of crystallites can be due to both the deformation and the increase in temperature (dominantly due to deformation). For PLLA, the temperature range can be, for example, 10-90° C. above Tg. Lower temperatures, (e.g., 10-30° C. above Tg), are preferred since smaller crystallites are formed.

In other embodiments, the temperature of the polymer construct during deformation can be the same as the temperature during the annealing step. The deformation process can induce growth of crystallites around nucleating agent particles and the nuclei formed during the annealing step. Growth of crystallites during deformation can occur even at temperatures at which there is little or no crystallite growth at quiescent conditions. As stated above, the schematic curve (B) for the crystal growth rate in FIG. 2 corresponds to quiescent conditions, and, thus, does not apply to the crystallite growth during deformation. The temperature of the polymer construct is desirably above Tg during deformation since as described below, Tg represents a transition from a vitreous state to a solid deformable or ductile state. Therefore, a temperature above Tg facilitates deformation of the polymer.

In still further embodiments, a temperature induced crystallite growth step and a deformation step can be performed sequentially. For example, the temperature can be increased to grow crystallites, followed by a deformation step at a selected temperature. Alternatively, a deformation step can be performed, followed by equilibrating the deformed construct at an increased temperature that allows crystallites to grow.

Heating and maintaining a temperature of a polymer construct at an annealing temperature or a crystallite growth temperature can be performed by various methods. For example, the construct in can be heated in a vacuum oven. Alternatively, a warm gas such as nitrogen, oxygen, air, argon, or other gas can be blown on the construct. The temperature of the construct can be maintained by known control methods.

Figure 5:
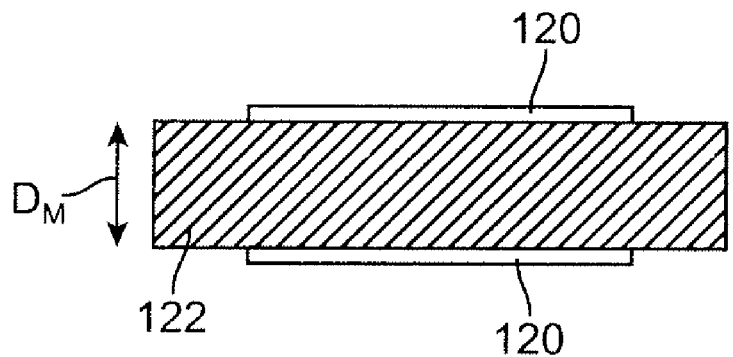
FIG. 5 depicts an axial cross-section of a polymer tube disposed over a mandrel with an inner diameter of the tube the same or substantially the same as an outer diameter of the mandrel.

A polymer construct may have a tendency to change shape upon heating. In particular a polymeric tube may tend to reduce in diameter or shrink upon heating. In some embodiments, the reduction in diameter of a polymer tube during the annealing step or temperature-induced crystal growth steps can be reduced or prevented. Reduction in diameter can be reduced or prevented by disposing a polymeric tube over a mandrel during the heating. The shrinkage of the tube is limited to the outside diameter of the mandrel. To prevent reduction in diameter, the inside diameter of the tube can be the same or substantially the same as the outside diameter of the mandrel. FIG. 5 illustrates this with an axial cross-section of a polymer tube 120 disposed over a mandrel 122. An inner diameter of tube 120 is the same or substantially the same as an outer diameter Dm of mandrel 122.

Figure 6A:
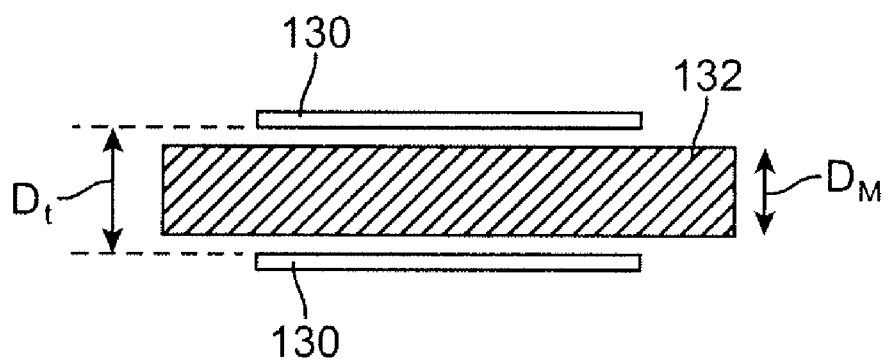
FIG. 6A depicts an axial cross-section of a polymer tube disposed over a mandrel with an inner diameter of the tube greater than an outer diameter of the mandrel.
Figure 6B:
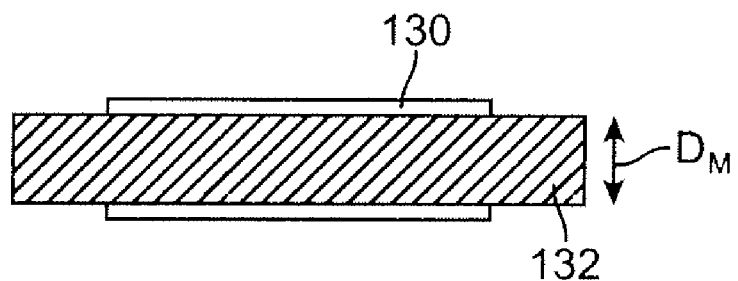
FIG. 6B shows the tube of FIG. 6A tube reduced in diameter due to heating.

To reduce shrinkage, the mandrel has an outside diameter less than the inside diameter of the polymer tube. FIG. 6A depicts this with an axial cross-section of a polymer tube 130 disposed over a mandrel 132. An inner diameter Dt of tube 130 is greater than an outer diameter Dm of mandrel 132. FIG. 6B shows that as tube 130 is heated during annealing or crystallite growth, tube 130 can reduce in diameter, but that the reduction in diameter is limited to the outer diameter Dm of the mandrel.

In further embodiments, shrinkage can be reduced or prevented by maintaining an increased pressure within the tube. For example, the polymer tube can be disposed in a mold, e.g., glass, and the internal pressure is increased during heating by blowing a gas in the tube.

Figure 7A:
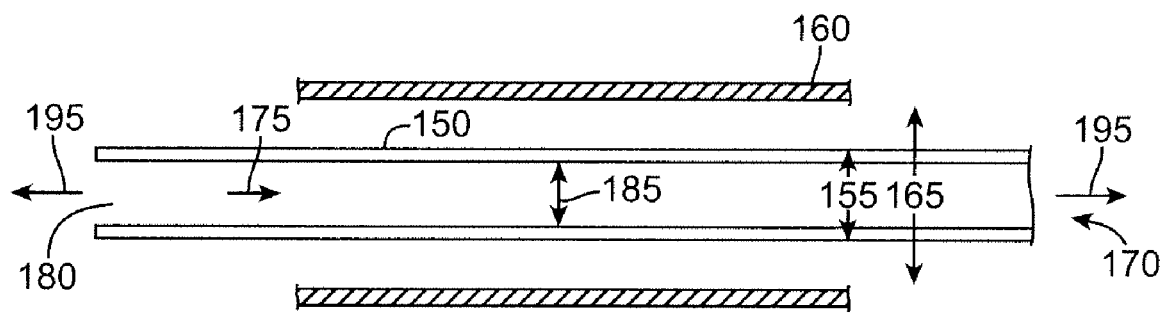
FIG. 7A depicts an axial cross-section of a polymeric tube positioned within a mold.
Figure 7B:
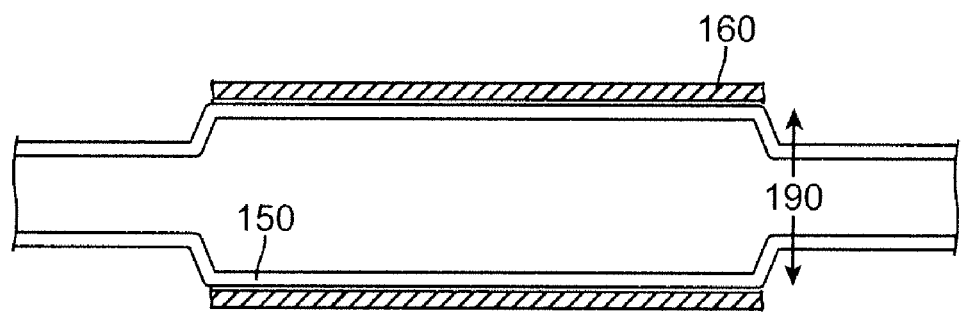
FIG. 7B depicts the polymeric tube of FIG. 7A in a radially deformed state.

As described above, a polymeric tube can be radially deformed using blow molding. FIGS. 7A-B illustrate an exemplary embodiment of deforming a polymeric tube using blow molding. FIG. 7A depicts an axial cross-section of a polymeric tube 150 with an outside diameter 155 positioned within a mold 160. Mold 160 limits the radial deformation of polymeric tube 150 to a diameter 165, the inside diameter of mold 160. Polymer tube 150 may be closed at a distal end 170 which may be open in subsequent manufacturing steps. A fluid is conveyed, as indicated by an arrow 175, into an open proximal end 180 of polymeric tube 150. A tensile force 195 can be applied at proximal end 180 and a distal end 170.

Polymeric tube 150 may be heated by heating the fluid to a temperature above ambient temperature prior to conveying the gas into polymeric tube 150. Alternatively, the polymeric tube may be heated by heating the exterior of mold 160 by blowing a warm gas on the mold. The tube may also be heated by a heating element in the mold.

The increase in pressure inside of polymer tube 150 facilitated by the increase in temperature of the polymeric tube causes radial deformation of polymer tube 150, as indicated by an arrow 185. FIG. 7B depicts polymeric tube 150 in a deformed state with an outside diameter 190 within mold 160.

In some embodiments, the tube may be expanded at the same time or about the same time along an entire axial length of the tube. In this case, the tube is heated uniformly or close to uniformly along the axial length. The tube then expands along this length when it reaches an expansion temperature close to or above Tg. Alternatively, the tube can expand sequentially along an axial length. In this case, a heating nozzle may translate along the axial length, heating the tube as its translates. The tube then expands as the nozzle translates and heats the tube.

Furthermore, the tube may be expanded to a target diameter. In one embodiment, the target diameter may be the diameter at which a stent pattern is formed by laser machining the tube. The target diameter can also correspond to the diameter of a stent prior to crimping. The degree of radial deformation may be quantified by a blow-up ratio or radial draw ratio:

$$\frac{\text{Inside Diameter of Deformed Tube}}{\text{Original Inside Diameter of Tube}}$$

In some embodiments, the radial draw ratio of a polymeric tube for use in fabricating a stent may be between about 1 and 10, or more narrowly between about 2 and 6. Similarly, the degree of axial deformation may be quantified by an axial draw ratio:

$$\frac{\text{Length of Deformed Tube}}{\text{Original Length of Tube}}$$

As described above, the crystal growth may be achieved through deformation, an increased temperature, or both.

Increasing crystallinity from an amorphous or low crystallinity construct allows more control of the crystallinity, crystal size, and nucleation density obtained through crystal growth, in particular, during expansion. All or most of the crystallinity can be tuned or controlled during the crystal growth step since all or most of the crystals grow from the nuclei from annealing or nucleating agent. As a result, all or most of the crystallinity is formed from uniformly dispersed nuclei or nucleating agent with a high nucleation density.

In addition, all or most of the crystallinity include crystals with a relatively uniform distribution of crystal size, since they are formed through growth around nucleating agent or nuclei. The crystallite size in polymers is rarely completely uniform. Rather there is a distribution in sizes resulting in a melting point range where the smaller crystallites melt at lower temperature than larger ones. The largest melts at the highest temperature since the surface to volume ratio is lowest.

Additionally, a construct that is amorphous or very low crystallinity provides for greater reproducibility of a final processed construct with respect to microstructure and mechanical properties. Microstructure includes crystal size, crystal density, crystal orientation, amorphous orientation, and crystal shape. Polymer constructs, such as polymer tubes, made from extrusion or injection molding typically have crystallinity of at least 10%, 20%, or greater than 30%, which limits the freedom of morphology and microstructure control during crystal growth, for example, during deformation or expansion. For example, the crystal size increases very quickly during deformation due to a very fast crystal growth rate compared to relatively slow nucleation rate. Therefore, presence of nuclei or a nucleating agent greatly facilitates high nucleation density and smaller crystal size.

Furthermore, the crystallinity and the microstructural properties of polymer constructs produced from different runs of extrusion and injection molding can vary. This can be attributed to the dependence of crystallinity and microstructure of the construct on the processing parameters of these processes and insufficient control of such parameters during processing.

Embodiments of the present invention further include forming a polymer construct, such as a polymer tube, from extrusion having amorphous structure or very low crystallinity through control of extrusion processing conditions and parameters. The polymer construct can include nucleating agent dispersed in the polymer tube or can be free of added nucleating agent.

In general, extrusion refers to the process of conveying a polymer melt through an extruder and forcing the polymer melt through a die that imparts a selected shape to the polymer exiting the extruder. In the case of tubing extrusion, the polymer melt (extrudate) forced through the die forms a cylindrical film in the shape of a tube. The film is cooled and drawn axially to form the final tube product.

An extruder generally includes a barrel through which a polymer melt is conveyed from an entrance to an exit port. The polymer can be fed to the extruder barrel as a melt or in a solid form below its melting temperature. The solid polymer is melted as it is conveyed through the barrel. The polymer in the extruder barrel is heated to temperatures above the melting temperature (Tm) of the polymer and exposed to pressures above ambient. The polymer within the barrel is conveyed or pumped, for example, through the use of rotating screws. Representative examples of extruders for use with the present invention may include single screw extruders, intermeshing co-rotating and counter-rotating twin-screw extruders and other multiple screw plasticating extruders.

The polymer melt exits the extruder to a die placed at the end of the extruder barrel. A die generally refers to a device having an orifice with a specific shape or design geometry that it imparts to a polymer melt pumped from an extruder. In the case of tubing extrusion, the die has a circular-shaped orifice that imparts a cylindrical shape to the polymer melt exiting the die. The function of the die is to control the shape of the polymer melt by delivering polymer melt to the orifice. The polymer melt can be delivered at a constant rate, temperature, and pressure.

After the polymer leaves the die, it swells to compensate for the compression that takes place during processing. As the polymer leaves the die, it is stretched and drawn down by a conveyor or puller during cooling. "Draw down" refers to reducing the size of the polymer by stretching. For example, a tube is stretched longitudinally which reduces the diameter of the tube. The amount of draw down is defined as the "draw down ratio," which is the ratio of the area of the die opening to the final cross-sectional area of the tube. The draw down ratio can be at least three times the original extruded shape.

Crystallinity in extruded polymeric tubing can arise from several sources. Several parameters in a tubing extrusion process influence the properties, including crystallinity, in the extruded tubing. Several embodiments include adjusting parameters of the extrusion process to reduce or eliminate such sources and thus, the crystallinity in an extruded tube. These parameters include, but are not limited to, the temperature profile of the extruder, screw geometry, screw speed, tubing cooling rate, the puller speed, the air pressure in extruder, and the area draw down ratio.

The presence of unmelted crystals in a polymer melt exiting a die can result in crystallinity in a formed tube. A process for forming a tube with an amorphous structure or very low crystallinity can include completely removing crystallinity in the extruder from polymer resin fed into the extruder. A polymer resin, typically obtained from a commercial supplier, for feeding into an extruder may have extremely high crystallinity (e.g., approximately 60-65%). The process can include completely melting the resin in the extruder to remove all crystalline phase. This can be achieved by adjusting one or more processing parameters of the extruder.

For example, complete removal of the crystalline phase from the resin can be achieved by a suitably high extrusion temperature. The temperature should be high enough to melt the crystal, but below a temperature that would degrade the polymer. An exemplary temperature in the extruder is at least 20° above the Tm of the polymer. For example, temperature range for PLLA extrusion is 200-225° C. for PLLA. Below this temperature range, unmelted crystals are likely to exist in the extruder and result in crystallinity in the formed tube.

The melting efficiency can be facilitated by optimizing screw geometry. Both extruder design parameters and other parameters can be modified, followed by review of the quality of extrudate. Extruder design parameters that can be modified include the screw design, such as compression ratio, feed length, and screw L/D, helix angle. Process parameters that can be adjusted include the screw rpm, pressure, and drawdown.

The melting efficiency can further be facilitated by increasing shear stress in the mixing and melting zone of the extruder, for example, by using a twin screw extruder or by a longer residence time.

Other sources of crystallinity in an extruded tube is insufficient homogeneity of the polymer melt and chain orientation in the polymer melt in the extruder and polymer melt exiting the extruder. A polymer melt may have localized regions which a lack homogeneity. Melt homogeneity may be characterized by a homogeneous temperature within a volume element, little or not chain elongation, and no presence of a polymer gel. If regions of homogeneity are not homogenized, crystallinity may develop upon solidification of the polymer.

The stretching of polymer chains to form any chain orientation before/after exiting the die would cause strain-induced crystallization upon solidification of the polymer. Therefore, the chain orientation should be minimized or prevented before polymer melt exits the die, and the circumferential/longitudinal chain stretch should be minimized or prevented during the cooling period from melt stage to final stage once the polymer melt exits the die. The drawdown ration is between 1-4 preferably, less than 1.

Melt inhomogeneity and the effects of chain stretch can be minimized or eliminated before the molten polymer comes out of the die by adding a mixing section at the end of the extruder screw or before the die. The chain stretch outside of the extruder can be minimized or eliminated by adjusting the screw speed, the puller speed, gas blowing pressure used for cooling, and draw down ratio. The screw speed, puller speed, and drawdown ratio can be reduced to minimize the chain stretch. A lower gas blowing pressure will also minimize chain stretch.

The process can further include quenching the extruded tubing that exits the die to prevent the recrystallization during the cooling process. Quenching the tube refers to an extremely rapid cooling or extremely rapid reduction of the temperature of the polymer from a temperature above Tm of the polymer to below Tg of the polymer. The quenching can be achieved by contacting the exiting polymer with a chilled quenching medium such as chilled water or circulation or chilled gases. The rapid cooling can be facilitated by decreasing the distance between the extruder die and the quenching medium, using a chilled gas to cool the inside of tubing, or a combination thereof. A fast quenching process is extremely important to obtain PLLA tubing with low crystallinity when nucleating agent is used.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress—strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

EXAMPLE

The example set forth below are for illustrative purposes only and are in no way meant to limit the invention. The following example is given to aid in understanding the invention, but it is to be understood that the invention is not limited to the particular example. The Example below is provided by way of illustration only and not by way of limitation. The parameters and data are not to be construed to limit the scope of the embodiments of the invention.

PLLA Stent Preparation by Increasing PLLA Nuclei Through Annealing Before Tubing Expansion Step 1 (tubing extrusion): PLLA material is extruded in a single screw extruder at 200° C.-220° C. and the tubing is quickly quenched in cold water or other cooling medium. The size of the extruded tubing is set at about 0.02" for inside diameter (ID) and 0.06" for outside diameter (OD).

Step 2 (tubing Annealing): The extruded tubing is annealed at a temperature between 60 to 75° C. for 30 min to 3 h to create a certain amount of PLLA nuclei.

Step 3 (tubing expansion): The annealed tubing is placed in a glass mold and expanded at about 170° F. to 200° F. to obtain biaxial orientation and higher crystallinity. Its final ID and OD are set at about 0.12" and 0.13", respectively.

Step 4 (stent preparation): A stent is cut from the expanded tubing using a femto-second laser, crimped down to a small size (0.05") on a balloon catheter, and sterilized by electron beam at a dose of 25+/−5 kGy.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:
   forming a polymeric tube comprising nucleating agent particles dispersed within the polymer, wherein the nucleating agent particles comprise insoluble particles which provide nuclei for heterogeneous crystallization to increase nucleation density, wherein crystal growth is minimized or prevented during formation of the tube so that the polymer of the formed tube has a crystallinity of less than 5%;
   annealing the polymeric tube at a temperature in a temperature range of above Tg and below Tm with no crystal growth during a selected annealing time of greater than 1 hr;
   after annealing, inducing and allowing crystal growth around the nucleating agent particles dispersed within the polymeric tube to obtain a desired crystallinity,
   wherein the crystal growth is induced by radially deforming the polymer tube to provide circumferential orientation in the polymeric tube; and
   fabricating a stent from the tube after the crystal growth.

2. The method of claim 1, wherein the polymer of the polymeric tube is selected from the group consisting of PLLA and PGA.

3. The method of claim 1, wherein the polymer of the polymeric tube is PLLA.

4. The method of claim 1, wherein the polymeric tube is completely or near completely amorphous prior to inducing crystal growth.

5. The method of claim 1, wherein forming the polymeric tube comprises fabricating the polymeric tube using extrusion which includes quenching the polymeric tube as it exits an extruder to a temperature below Tg of the polymeric tube to prevent recrystallization.

6. The method of claim 1, wherein the polymer of the polymeric tube is bioabsorbable.

7. The method of claim 1, wherein the annealing of the polymeric tube is at a temperature in a temperature range of Tg to Tg+5° C.

8. A method of making a stent comprising:

forming a polymeric tube comprising nucleating agent particles dispersed within the polymer, wherein the nucleating agent particles comprise insoluble particles which provide nuclei for heterogeneous crystallization to increase nucleation density, wherein crystal growth is minimized or prevented during formation of the tube so that the polymer of the formed tube has a crystallinity of less than 5%;

annealing the polymeric tube at a temperature in a temperature range of above Tg and below Tm with no crystal growth during a selected annealing time of greater than 1 hr;

after annealing, inducing and allowing crystal growth around the nucleating agent particles dispersed within the polymeric tube to obtain a desired crystallinity, wherein the crystal growth is induced by increasing the temperature of the polymeric tube; and fabricating a stent from the tube after the crystal growth.

9. The method of claim 8, wherein the polymer of the polymeric tube is PLLA.

* * * * *